United States Patent [19]

Endo

[11] Patent Number: 4,472,989
[45] Date of Patent: Sep. 25, 1984

[54] BLADE HOLDER FOR MICROTOME FOR CUTTING FROZEN SAMPLE

[76] Inventor: Hidetoshi Endo, 1599-2, Hidase, Seki City, Gifu Prefecture, Japan

[21] Appl. No.: 442,432

[22] Filed: Nov. 17, 1982

[30] Foreign Application Priority Data

Nov. 28, 1981 [JP] Japan .................. 56-177250[U]

[51] Int. Cl.³ .................................................. G01N 1/06
[52] U.S. Cl. .......................................... 83/162; 83/700; 83/856; 83/915.5
[58] Field of Search ................ 83/698, 699, 700, 870, 83/915.5, 856, 162

[56] References Cited

U.S. PATENT DOCUMENTS 4,024,779  5/1977  Taugner ........................ 83/915.5
4,207,790  6/1980  Endo ................................ 83/698

FOREIGN PATENT DOCUMENTS 253250  3/1967  Austria .
2140796  2/1973  Fed. Rep. of Germany .

Primary Examiner—James M. Meister
Attorney, Agent, or Firm—Wenderoth, Lind & Ponack

[57] ABSTRACT

A blade holder for microtome for cutting frozen samples, in which a replaceable blade is clamped between a holder body and an urging member, and which comprises a bracket mounted on a rear portion of the holder body, a rotary shaft supported in the bracket to extend parallel to the holder body, an anti-roll plate secured to the front end of a shaft member penetrating a see-through hole formed in the rotary shaft so that the anti-roll plate is disposed above the urging member, said anti-roll plate being spring biased in a direction to cause its displacement to the front, and a nut fitted on the rear end of the shaft member.

2 Claims, 2 Drawing Figures

BLADE HOLDER FOR MICROTOME FOR CUTTING FROZEN SAMPLE

BACKGROUND OF THE INVENTION

1. Field of the Invention

This invention relates to a blade holder for microtome for cutting frozen samples, and it seeks to permit ready positional adjustment of an anti-roll plate for preventing sample pieces to be cut from being rolled.

2. Prior Art

A blade holder for microtome for cutting microscope samples are well known and disclosed in U.S. Pat. No. 4,207,790 filed by the same inventor of this application.

The microtome which adopts the blade holder serves to cut a sample wrapped in paraffin to the thickness of several microns to several 10 microns. When a frozen sample is cut using a microtome for cuttng a sample wrapped in paraffin, the cut sample pieces are liable to be rolled, and therefore correct cut sample pieces can not be obtained. Accordingly, the usual microtome is provided with an anti-roll plate. The anti-roll plate has to be adjusted in position in accordance with the thickness of the sample to be cut. With the prior art microtome the anti-roll plate is installed on and in the neighborhood of a blade mount of microtome for cutting frozen samples, and its positional adjustment has been very troublesome. In addition, the anti-roll plate has to be adjusted afresh every time the blade holder is replaced. With the microtome the sample structure is destroyed if the cutting property of the blade is deteriorated. Therefore, it is necessary to cut sample always with a blade having excellent cutting property. Therefore, the blade has to be frequently removed for replacement. However, since with the prior art microtome the anti-roll plate is installed on and in the neighborhood of the blade mount of microtome for cutting frozen samples, the positional adjustment of the anti-roll plate has to be done every time the blade is replaced, and the adjustment is very troublesome and time-consuming.

SUMMARY OF THE INVENTION

According to the invention, an anti-roll plate is mounted on a blade holder so that the positional adjustment of the anti-roll plate can be made with the blade holder removed from a blade mount.

DETAILED DESCRIPTION OF THE INVENTION

Figure 1:
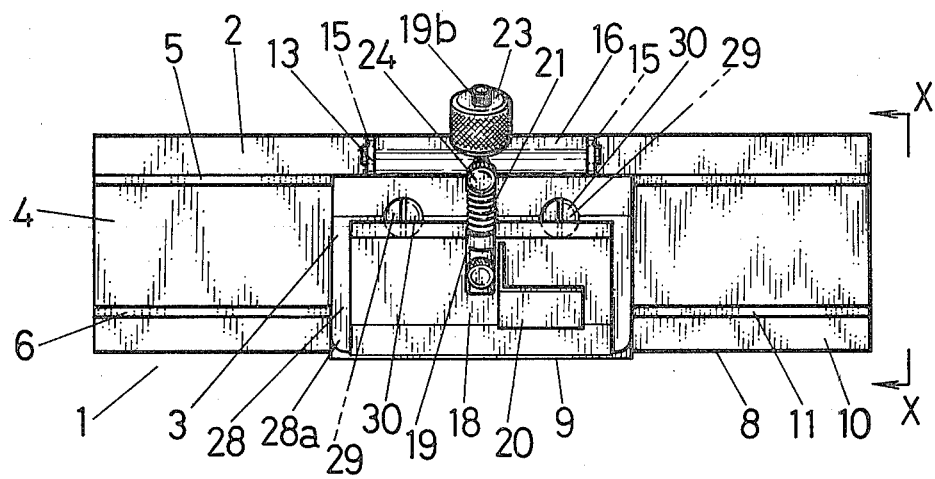
FIG. 1 is a plan view showing one embodiment of the invention.
Figure 2:
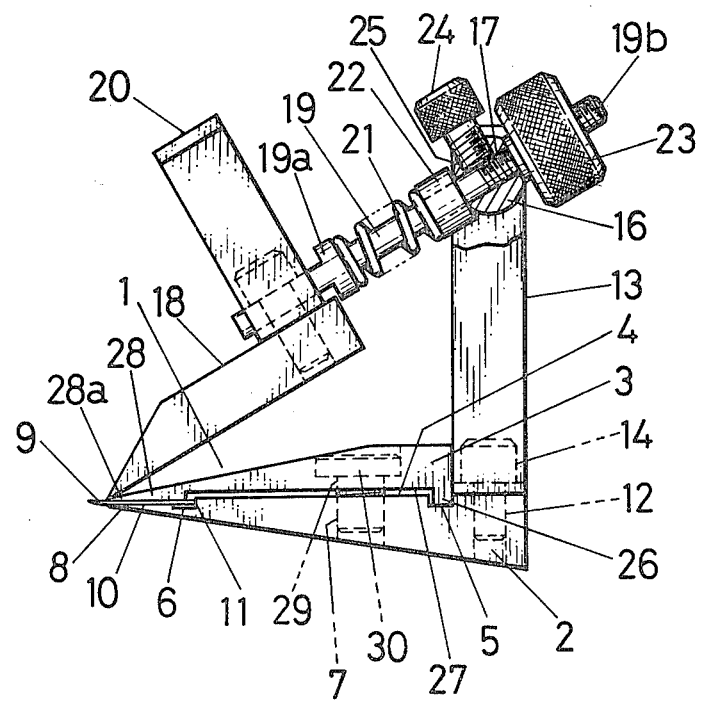
FIG. 2 is an enlarged-scale side view, partly broken away, taken in the direction of arrows X in FIG. 1.

Referring to FIGS. 1 and 2, a blade holder 1 which is removable mounted on a blade mount of a microtome includes a body 2 and an urging member 3. The body 2 is wedge-like in form or has a triangular sectional profile. Its top surface 4 is provided with parallel straight grooves 5 and 6, one extending in a rear portion and the other extending in a front portion. It is further provided with two threaded holes 7 formed between the grooves 5 and 6 and spaced apart a given distance in the lengthwise direction. The body 2 further has a smooth mount surface 10 formed between its sharp acute front edge 8 and the groove 6. The level of the mount surface 10 is reduced by an amount corresponding to the thickness of a blade 9. When the blade 9 is set on the mount surface 10, the rear edge of the blade 9 is held in uniform contact with a side wall 11 of the groove 6.

The rear portion of the body 2 is provided at the top with one or more threaded holes 12. A channel-shaped bracket 13 is secured to the body 2 by screws 14 screwed in the threaded holes 12. The bracket 13 is open at the top, and it is provided at the opposite ends with shaft holes 15, in which the opposite ends of a rotary shaft 16 are supported. The rotary shaft 16 is provided at its intermediate portion in the lengthwise direction with a see-through hole 17, through which a support shaft 19 for an anti-roll plate 18 penetrates. The support shaft 19 has an increased diameter end portion 19a and also has a threaded portion 19b formed at the other end. The large diameter portion 19a supports the anti-roll plate 18 secured thereto. The anti-roll plate 18 is wedge-shaped in form, with the thickness of its front end portion gradually reducing as one goes toward the front end. It is mostly made of a transparent plastic material. It is provided with a grip 20 bent to a desired shape. A spring 21 and a collar 22 are fitted on the shaft 19. The threaded portion 19b of the shaft 19 is inserted in the hole 17 and screwed by a nut 23 and is biased by the spring 21. A set screw 24 is screwed in the threaded hole 25 formed in the rotary shaft 16 with its tip in forced with the shaft 19.

The urging member 3 is made of flourine resin and provided with a plastic coating in black colour. The urging member 3 has a ridge 26 formed on the underside and having a width corresponding to the width of the grooves 5 formed in the body 2. It also has an urging section 28 extending on the side of a recessed portion 27 opposite the ridge 26. The top surface of the urging section 28 has a given angle of inclination. The front edge 28a of the urging member 28 is adapted to be aligned to the front edge 8 of the body 2 when the ridge 26 is received in the groove 5. The urging member 3 is formed at positions corresponding to the threaded holes 7 of the body 2 with see-through holes 29.

For installing the blade 9 on the holder 1 having the construction described above, the ridge 26 of the urging member 3 is inserted in the groove 5 of the body 2, and screws 30 are passed through the see-through holes 29 and screwed in the threaded holes 7. With the screws 30 held loose, the blade 9 is inserted into between the urging member 28 and mount surface 10. Then, with the rear edge of the blade 9 held in contact with the side wall 11 the screws 30 are clamped to clamp the blade 9 between the urging section 28 and mount surface 10. In this state, the cutting edge of the blade 9 projects a predetermined dimension form the front edge of the urging member 3.

The positional adjustment of the anti-roll plate 18 is desirably carried out before mounting the holder 1 on the blade mount of the microtome. For the adjustment, a nut 23 is turned with the set screw 24 held loose, thereby causing axial displacement of the shaft 19. The front edge of the anti-roll plate 19 slightly projects from the front edge of the urging member 28. Cellophane tape, metal foil, etc. is applied to the opposite ends of the underside of the front portion of the anti-roll plate 18, and a slight gap capable of passage of a sample slice through it is formed between the top surface of the blade 9 and the front edge of the central portion of the anti-roll plate 18. This gap is set in correspondence to the thickness of the thickness of the sample piece to be cut. If the thickness of the sample piece is increased, the gap is increased by applying several cellophane tapes or metal foils in the laminated form.

The construction described in the foregoing according to the invention has the following advantages.

Since the anti-roll plate is mounted on the blade holder, it can be removed together with the blade holder from the blade mount. Thus, when adjusting the position of the anti-roll plate for the first time in correspondence to the thickness of the sample piece, the adjustment can be done with the blade holder removed from the blade mount to that it can be readily carried out compared to the case of the prior art product where the anti-roll plate is securely mounted on the blade mount.

Further, when the cutting property of the blade is deteriorated, it is necessary to replace the blade alone. Further, since the blade is always correctly positioned with respect to the blade holder, once the position of the anti-roll plate is adjusted, there is no need of making any positional adjustment of the anti-roll plate every time the blade is replaced.

To produce an unsticky surface by using an fluorine resin for urging member, a plastic coating is provided, so that the cut pieces can slip down the surface without being attached thereto. This is very important when producing accurate cutting samples successibely under continuous cutting condition. The plastic coating is black in colour and permits ready judgement of the thickness of the cut pieces and the quality thereof. Ultimately, it is possible to obtain high quality samples reliably and quickly.

What is claimed is:

1. A blade holder for microtome for cutting frozen samples in which a replaceable blade is clamped between a holder body and an urging member, comprising:

a bracket mounted on a rear portion of said holder body;

a rotary shaft supported in said bracket to extend parallel to said holder body, said rotary shaft being provided at the middle portion in the lengthwise direction with a see-through hole;

an anti-roll plate secured to the front end of a shaft member penetrating said see-through hole so that said anti-roll plate is disposed above said urging member, said anti-roll plate being spring biased in a direction to cause its displacement to the front; and a nut fitted on the rear end of said shaft member.

2. A blade holder for microtome for cutting frozen samples as set forth in claim 1, wherein the urging member is provided with a plastic coating in black colour.

* * * * *